(12) United States Patent
Schneid et al.

(10) Patent No.: US 7,585,325 B2
(45) Date of Patent: Sep. 8, 2009

(54) INTERVERTEBRAL IMPLANT

(75) Inventors: Susanne Schneid, Tuttlingen (DE); Robert Schultz, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 405 days.

(21) Appl. No.: 11/153,798

(22) Filed: Jun. 15, 2005

(65) Prior Publication Data

US 2006/0020341 A1    Jan. 26, 2006

(30) Foreign Application Priority Data

Jun. 16, 2004    (DE) .................. 10 2004 028 967

(51) Int. Cl.
*A61F 2/44* (2006.01)
(52) U.S. Cl. ............... 623/17.14; 623/17.15; 623/17.11
(58) Field of Classification Search ............. 606/61, 606/17.11; 623/16.11, 17.11–17.16
See application file for complete search history.

(56) References Cited

U.S. PATENT DOCUMENTS

| | | | |
|---|---|---|---|
| 3,266,113 A | 8/1966 | Flanagan, Jr. | |
| 3,426,364 A | 2/1969 | Lumb | |
| 3,867,728 A | 2/1975 | Stubstad et al. | |
| 3,875,595 A | 4/1975 | Froning | |
| 4,309,777 A | 1/1982 | Patil | |
| 4,759,766 A | 7/1988 | Buettner-Janz et al. | |
| 4,759,769 A | 7/1988 | Hedman et al. | |
| 4,848,555 A | 7/1989 | Riese et al. | |
| 4,863,476 A | 9/1989 | Shepperd | |
| 4,863,477 A | 9/1989 | Monson | |
| 4,911,718 A | 3/1990 | Lee et al. | |
| 5,002,576 A | 3/1991 | Fuhrmann et al. | |
| 5,037,438 A | 8/1991 | Davidson | |
| 5,119,531 A | 6/1992 | Berger et al. | |
| 5,122,130 A | 6/1992 | Keller | |
| 5,123,926 A | 6/1992 | Pisharodi | |
| 5,192,327 A | 3/1993 | Brantigan | |
| 5,201,101 A | 4/1993 | Rouser et al. | |
| 5,236,460 A | 8/1993 | Barber | |
| 5,258,031 A | 11/1993 | Salib et al. | |
| 5,306,308 A | 4/1994 | Gross et al. | |

(Continued)

FOREIGN PATENT DOCUMENTS

DE    2 263 842    7/1974

(Continued)

OTHER PUBLICATIONS

Partial European Search Report dated Aug. 22, 2005; Berlin.

(Continued)

*Primary Examiner*—Eduardo C Robert
*Assistant Examiner*—Tara R George
(74) *Attorney, Agent, or Firm*—RatnerPrestia

(57) ABSTRACT

In an intervertebral implant with a top contacting element, a bottom contacting element and arranged between these a core which with an upper, spherical bearing surface engages a spherical bearing socket, having the same radius, of the top contacting element and with a lower, spherical bearing surface engages a spherical bearing socket, having the same radius, of the bottom contacting element, in order to improve the kinematics and the endurance, it is proposed that the radius of the bearing surface and of the bearing socket receiving it differ on opposing sides of the core at least by the factor 5.

20 Claims, 4 Drawing Sheets

U.S. PATENT DOCUMENTS

| | | | |
|---|---|---|---|
| 5,314,477 A | 5/1994 | Marnay | |
| 5,370,697 A | 12/1994 | Baumgartner | |
| 5,401,269 A * | 3/1995 | Buttner-Janz et al. | 623/17.15 |
| 5,425,773 A | 6/1995 | Boyd et al. | |
| 5,507,816 A | 4/1996 | Bullivant | |
| 5,534,030 A | 7/1996 | Navarro et al. | |
| 5,545,227 A | 8/1996 | Davidson et al. | |
| 5,556,431 A | 9/1996 | Buttner-Janz | |
| 5,562,738 A | 10/1996 | Boyd et al. | |
| 5,674,294 A | 10/1997 | Bainville et al. | |
| 5,674,296 A | 10/1997 | Bryan et al. | |
| 5,676,635 A | 10/1997 | Levin | |
| 5,676,701 A * | 10/1997 | Yuan et al. | 623/17.15 |
| 5,683,465 A * | 11/1997 | Shinn et al. | 623/17.14 |
| 5,702,449 A | 12/1997 | McKay | |
| 5,782,830 A | 7/1998 | Farris | |
| 5,782,832 A | 7/1998 | Larsen et al. | |
| 5,824,094 A | 10/1998 | Serhan et al. | |
| 5,827,328 A | 10/1998 | Buttermann | |
| 5,865,846 A | 2/1999 | Bryan et al. | |
| 5,888,226 A | 3/1999 | Rogozinski | |
| 5,888,227 A | 3/1999 | Cottle | |
| 5,893,889 A | 4/1999 | Harrington | |
| 5,989,291 A | 11/1999 | Ralph et al. | |
| 6,001,130 A | 12/1999 | Bryan et al. | |
| 6,013,103 A | 1/2000 | Kaufman et al. | |
| 6,019,792 A | 2/2000 | Cauthen | |
| 6,019,793 A | 2/2000 | Perren et al. | |
| 6,039,763 A | 3/2000 | Shelokov | |
| 6,063,121 A | 5/2000 | Xavier et al. | |
| 6,083,225 A | 7/2000 | Winslow et al. | |
| 6,113,637 A | 9/2000 | Gill et al. | |
| 6,113,639 A | 9/2000 | Ray et al. | |
| 6,127,597 A | 10/2000 | Beyar et al. | |
| 6,139,579 A | 10/2000 | Steffee et al. | |
| 6,146,421 A * | 11/2000 | Gordon et al. | 623/17.15 |
| 6,156,067 A | 12/2000 | Bryan et al. | |
| 6,162,252 A | 12/2000 | Kuras et al. | |
| 6,176,881 B1 | 1/2001 | Schar et al. | |
| 6,193,757 B1 | 2/2001 | Foley et al. | |
| 6,200,322 B1 | 3/2001 | Branch et al. | |
| 6,206,923 B1 | 3/2001 | Boyd et al. | |
| 6,210,442 B1 | 4/2001 | Wing et al. | |
| 6,228,118 B1 * | 5/2001 | Gordon | 623/17.14 |
| 6,231,609 B1 | 5/2001 | Mehdizadeh | |
| 6,277,149 B1 | 8/2001 | Boyle et al. | |
| 6,296,664 B1 | 10/2001 | Middleton | |
| 6,348,071 B1 | 2/2002 | Steffee et al. | |
| 6,367,128 B1 | 4/2002 | Galkiewicz et al. | |
| 6,368,350 B1 | 4/2002 | Erickson et al. | |
| 6,395,032 B1 | 5/2002 | Gauchet | |
| 6,419,704 B1 | 7/2002 | Ferree | |
| 6,419,706 B1 | 7/2002 | Graf | |
| 6,443,987 B1 | 9/2002 | Bryan | |
| 6,443,990 B1 | 9/2002 | Aebi et al. | |
| 6,468,310 B1 | 10/2002 | Ralph et al. | |
| 6,491,726 B2 | 12/2002 | Pappas | |
| 6,494,915 B1 | 12/2002 | Villar Gonzalez et al. | |
| 6,517,580 B1 * | 2/2003 | Ramadan et al. | 623/17.15 |
| 6,520,996 B1 | 2/2003 | Manasas et al. | |
| 6,524,341 B2 | 2/2003 | Lang et al. | |
| 6,527,804 B1 | 3/2003 | Gauchet et al. | |
| 6,527,806 B2 | 3/2003 | Ralph et al. | |
| 6,530,955 B2 | 3/2003 | Boyle et al. | |
| 6,533,818 B1 | 3/2003 | Weber et al. | |
| 6,540,785 B1 * | 4/2003 | Gill et al. | 623/17.14 |
| 6,558,424 B2 | 5/2003 | Thalgott | |
| 6,562,072 B1 | 5/2003 | Fuss et al. | |
| 6,572,653 B1 | 6/2003 | Simonson | |
| 6,575,899 B1 | 6/2003 | Foley et al. | |
| 6,579,320 B1 | 6/2003 | Gauchet et al. | |
| 6,579,321 B1 | 6/2003 | Gordon et al. | |
| 6,582,466 B1 | 6/2003 | Gauchet | |
| 6,582,468 B1 | 6/2003 | Gauchet | |
| 6,607,558 B2 | 8/2003 | Kuras | |
| 6,610,092 B2 | 8/2003 | Ralph et al. | |
| 6,613,090 B2 | 9/2003 | Eckhof et al. | |
| 6,626,943 B2 | 9/2003 | Eberlein et al. | |
| 6,645,248 B2 | 11/2003 | Casutt | |
| 6,645,249 B2 | 11/2003 | Ralph et al. | |
| 6,656,224 B2 | 12/2003 | Middleton | |
| 6,666,889 B1 | 12/2003 | Commarmond | |
| 6,669,730 B2 | 12/2003 | Ralph et al. | |
| 6,669,732 B2 | 12/2003 | Serhan et al. | |
| 6,673,113 B2 | 1/2004 | Ralph et al. | |
| 6,682,562 B2 | 1/2004 | Viart et al. | |
| 6,706,068 B2 | 3/2004 | Ferree | |
| 6,719,796 B2 | 4/2004 | Cohen et al. | |
| 6,723,097 B2 | 4/2004 | Fraser et al. | |
| 6,723,127 B2 | 4/2004 | Ralph et al. | |
| 6,726,720 B2 | 4/2004 | Ross et al. | |
| 6,733,532 B1 | 5/2004 | Gauchet et al. | |
| 6,736,850 B2 | 5/2004 | Davis | |
| 6,740,117 B2 | 5/2004 | Ralph et al. | |
| 6,740,118 B2 | 5/2004 | Eisermann et al. | |
| 6,740,119 B2 | 5/2004 | Errico et al. | |
| 6,758,861 B2 | 7/2004 | Ralph et al. | |
| 6,764,515 B2 | 7/2004 | Ralph et al. | |
| 6,770,095 B2 | 8/2004 | Grinberg et al. | |
| 6,793,678 B2 | 9/2004 | Hawkins | |
| 6,802,867 B2 | 10/2004 | Manasas et al. | |
| 6,827,740 B1 | 12/2004 | Michelson | |
| 6,918,934 B2 | 7/2005 | Ralph et al. | |
| 6,936,071 B1 * | 8/2005 | Marnay et al. | 623/17.15 |
| 6,984,245 B2 | 1/2006 | McGahan et al. | |
| 6,986,789 B2 | 1/2006 | Schultz et al. | |
| 7,001,432 B2 * | 2/2006 | Keller et al. | 623/17.14 |
| 7,105,024 B2 * | 9/2006 | Richelsoph | 623/17.13 |
| 7,156,876 B2 * | 1/2007 | Moumene et al. | 623/17.13 |
| 7,179,294 B2 * | 2/2007 | Eisermann et al. | 623/17.15 |
| 7,198,644 B2 | 4/2007 | Schultz et al. | |
| 7,235,101 B2 * | 6/2007 | Berry et al. | 623/17.11 |
| 7,291,173 B2 | 11/2007 | Richelsoph et al. | |
| 7,326,250 B2 * | 2/2008 | Beaurain et al. | 623/17.14 |
| 2002/0016773 A1 | 2/2002 | Ohkuma et al. | |
| 2002/0022887 A1 | 2/2002 | Huene | |
| 2002/0035400 A1 | 3/2002 | Bryan et al. | |
| 2002/0107573 A1 | 8/2002 | Steinberg | |
| 2002/0111681 A1 | 8/2002 | Ralph et al. | |
| 2003/0009223 A1 | 1/2003 | Fehling et al. | |
| 2003/0010802 A1 | 1/2003 | Blaimschein et al. | |
| 2003/0014112 A1 | 1/2003 | Ralph et al. | |
| 2003/0055427 A1 | 3/2003 | Graf | |
| 2003/0065395 A1 | 4/2003 | Ralph et al. | |
| 2003/0069586 A1 | 4/2003 | Errico et al. | |
| 2003/0069640 A1 | 4/2003 | Ferreira et al. | |
| 2003/0069643 A1 | 4/2003 | Ralph et al. | |
| 2003/0074066 A1 | 4/2003 | Errico et al. | |
| 2003/0074067 A1 | 4/2003 | Errico et al. | |
| 2003/0074068 A1 | 4/2003 | Errico et al. | |
| 2003/0074069 A1 | 4/2003 | Errico et al. | |
| 2003/0074070 A1 | 4/2003 | Errico et al. | |
| 2003/0074071 A1 | 4/2003 | Errico et al. | |
| 2003/0074072 A1 | 4/2003 | Errico et al. | |
| 2003/0074073 A1 | 4/2003 | Errico et al. | |
| 2003/0074074 A1 | 4/2003 | Errico et al. | |
| 2003/0078590 A1 | 4/2003 | Errico et al. | |
| 2003/0078663 A1 | 4/2003 | Ralph et al. | |
| 2003/0078666 A1 | 4/2003 | Ralph et al. | |
| 2003/0135277 A1 | 7/2003 | Bryan et al. | |
| 2003/0176923 A1 | 9/2003 | Keller et al. | |
| 2003/0187454 A1 | 10/2003 | Gill et al. | |
| 2003/0187506 A1 | 10/2003 | Ross et al. | |
| 2003/0191534 A1 | 10/2003 | Viart et al. | |

| | | | | | | |
|---|---|---|---|---|---|---|
| 2003/0220691 A1 | 11/2003 | Songer et al. | DE | 203 11 400 | 10/2003 | |
| 2003/0229355 A1 | 12/2003 | Keller | DE | 203 13 183 U1 | 11/2003 | |
| 2003/0229358 A1 | 12/2003 | Errico et al. | DE | 697 22 244 | 12/2003 | |
| 2003/0233146 A1 | 12/2003 | Grinberg et al. | DE | 203 15 611 | 1/2004 | |
| 2003/0236520 A1 | 12/2003 | Lim et al. | DE | 203 15 613 | 1/2004 | |
| 2003/0236571 A1 | 12/2003 | Ralph et al. | DE | 20 2004 009 542 | 9/2004 | |
| 2004/0002761 A1 | 1/2004 | Rogers et al. | DE | 20 2004 014 119 | 12/2004 | |
| 2004/0002762 A1 | 1/2004 | Hawkins | EP | 0 282 161 | 9/1988 | |
| 2004/0010316 A1 | 1/2004 | William et al. | EP | 0 282 161 A1 | 9/1988 | |
| 2004/0024462 A1 | 2/2004 | Ferree et al. | EP | 0 471 821 | 2/1992 | |
| 2004/0034420 A1 | 2/2004 | Errico et al. | EP | 0 560 141 | 9/1993 | |
| 2004/0034421 A1 | 2/2004 | Errico et al. | EP | 0 634 157 | 1/1995 | |
| 2004/0034422 A1 | 2/2004 | Errico et al. | EP | 0 747 025 | 12/1996 | |
| 2004/0034424 A1 | 2/2004 | Errico et al. | EP | 0 948 299 | 10/1999 | |
| 2004/0034425 A1 | 2/2004 | Errico et al. | EP | 1 002 500 | 5/2000 | |
| 2004/0034426 A1 | 2/2004 | Errico et al. | EP | 1 103 237 A2 | 5/2001 | |
| 2004/0059318 A1 | 3/2004 | Zhang et al. | EP | 1 124 509 | 8/2001 | |
| 2004/0073310 A1 | 4/2004 | Moumene et al. | EP | 0 955 021 B1 | 9/2001 | |
| 2004/0073312 A1 | 4/2004 | Eisermann et al. | EP | 1 250 898 | 10/2002 | |
| 2004/0078079 A1 | 4/2004 | Foley | EP | 1 250 898 A1 | 10/2002 | |
| 2004/0083000 A1 | 4/2004 | Keller et al. | EP | 1 057 462 B1 | 4/2003 | |
| 2004/0093088 A1 | 5/2004 | Ralph et al. | EP | 1 344 507 | 9/2003 | |
| 2004/0098130 A1 | 5/2004 | Ralph et al. | EP | 1 344 508 | 9/2003 | |
| 2004/0098131 A1 | 5/2004 | Bryan et al. | EP | 1 344 508 A1 | 9/2003 | |
| 2004/0102849 A1 | 5/2004 | Ralph et al. | EP | 1 374 808 A1 | 1/2004 | |
| 2004/0111156 A1 | 6/2004 | Ralph et al. | EP | 1 421 922 A1 | 5/2004 | |
| 2004/0117021 A1 | 6/2004 | Biedermann et al. | EP | 1 188 423 B1 | 9/2004 | |
| 2004/0117022 A1 | 6/2004 | Marnay et al. | EP | 1 475 059 | 11/2004 | |
| 2004/0133278 A1 | 7/2004 | Marino et al. | EP | 1 263 352 B1 | 12/2004 | |
| 2004/0133281 A1 | 7/2004 | Khandkar et al. | FR | 2 694 882 | 2/1994 | |
| 2004/0143331 A1 | 7/2004 | Errico et al. | FR | 2 718 635 | 10/1995 | |
| 2004/0143332 A1 | 7/2004 | Krueger et al. | FR | 2 730 159 | 8/1996 | |
| 2004/0148027 A1 | 7/2004 | Errico et al. | FR | 2 799 116 | 4/2001 | |
| 2004/0158325 A1 | 8/2004 | Errico et al. | FR | 2 799 638 A1 | 4/2001 | |
| 2004/0158328 A1 | 8/2004 | Eisermann | FR | 2 824 261 | 11/2002 | |
| 2004/0167534 A1 | 8/2004 | Errico et al. | JP | 06178787 | 6/1994 | |
| 2004/0167536 A1 | 8/2004 | Errico et al. | WO | WO 94/04100 | 3/1994 | |
| 2004/0167537 A1 | 8/2004 | Errico et al. | WO | WO 95/26697 | 10/1995 | |
| 2004/0167626 A1 | 8/2004 | Geremakis et al. | WO | WO 99/05995 | 2/1999 | |
| 2004/0170342 A1 | 9/2004 | Galkiewicz | WO | WO 99/11203 | 3/1999 | |
| 2004/0193158 A1 | 9/2004 | Lim et al. | WO | WO 00/04851 | 2/2000 | |
| 2004/0220582 A1 | 11/2004 | Keller | WO | WO 00/13619 | 3/2000 | |
| 2004/0220668 A1 | 11/2004 | Eisermann et al. | WO | WO 00/23015 | 4/2000 | |
| 2004/0220670 A1 | 11/2004 | Eisermann et al. | WO | WO 00/35385 | 6/2000 | |
| 2004/0220677 A1 | 11/2004 | Delfosse et al. | WO | WO 00/53127 | 9/2000 | |
| 2004/0225362 A1 | 11/2004 | Richelsoph | WO | WO 00/64385 | 11/2000 | |
| 2004/0225363 A1 | 11/2004 | Richelsoph | WO | WO 01/01893 A1 | 1/2001 | |
| 2004/0225364 A1 | 11/2004 | Richelsoph et al. | WO | WO 01/01895 | 1/2001 | |
| 2004/0225365 A1 | 11/2004 | Eisermann et al. | WO | WO0101893 A1 * | 1/2001 | .............. 623/17.15 |
| 2004/0225366 A1 | 11/2004 | Eisermann et al. | WO | WO 01/18931 | 3/2001 | |
| 2004/0243238 A1 | 12/2004 | Arnin et al. | WO | WO 01/19295 | 3/2001 | |
| 2004/0243240 A1 | 12/2004 | Beaurain et al. | WO | WO 01/64140 | 9/2001 | |
| 2004/0249462 A1 | 12/2004 | Huang | WO | WO 01/68003 | 9/2001 | |
| 2005/0033438 A1 | 2/2005 | Schultz et al. | WO | WO 0164140 A1 | 9/2001 | |
| 2005/0043803 A1 | 2/2005 | Schultz et al. | WO | WO 01/93785 | 12/2001 | |
| 2005/0080487 A1 | 4/2005 | Schultz et al. | WO | WO 01/93786 | 12/2001 | |
| 2005/0080488 A1 | 4/2005 | Schultz | WO | WO 02/080818 | 10/2002 | |
| 2006/0036325 A1* | 2/2006 | Paul et al. ................. 623/17.14 | WO | WO 02/089701 | 11/2002 | |
| 2006/0036326 A1 | 2/2006 | Baumgartner et al. | WO | WO 03/003952 | 1/2003 | |
| | | | WO | WO 03/007779 | 1/2003 | |
| FOREIGN PATENT DOCUMENTS | | | WO | WO 03/007780 | 1/2003 | |
| | | | WO | WO 03/028595 | 4/2003 | |
| DE | 30 23 353 | 4/1981 | WO | WO 03/039400 | 5/2003 | |
| DE | 0 239 524 A1 | 10/1986 | WO | WO 03/047472 | 6/2003 | |
| DE | 90 00 094.3 | 3/1991 | WO | WO 03/075803 | 9/2003 | |
| DE | 90 00 94 U | 3/1991 | WO | WO 03/075804 | 9/2003 | |
| DE | 691 02 369 T2 | 1/1995 | WO | WO 03/084449 A1 | 10/2003 | |
| DE | 197 10 392 | 7/1998 | WO | WO 03/090648 A1 | 11/2003 | |
| DE | 299 11 422 U1 | 8/1999 | WO | WO 03/094806 A1 | 11/2003 | |
| DE | 198 16 832 | 1/2000 | WO | WO 03/099172 | 12/2003 | |
| DE | 101 52 567 | 5/2003 | WO | WO 2004/016205 | 2/2004 | |
| DE | 203 10 433 | 9/2003 | WO | WO 2004/019828 | 3/2004 | |
| DE | 203 10 432 U1 | 10/2003 | WO | WO 2004/026186 | 4/2004 | |

| WO | WO 2004/039285 | 5/2004 |
| WO | WO 2004/041129 | 5/2004 |
| WO | WO 2004/041131 | 5/2004 |
| WO | WO 2004/054475 | 7/2004 |
| WO | WO 2004/054476 | 7/2004 |
| WO | WO 2004/054478 | 7/2004 |
| WO | WO 2004/054480 | 7/2004 |
| WO | WO 2004/073561 | 9/2004 |
| WO | WO 2004/084774 | 10/2004 |

OTHER PUBLICATIONS

Szpalski, Marek, Gunzburg, Robert, and Mayer, Michael, "Spine Arthroplasty: A Historical Review", Eur Spine J (2002), 11 (Suppl. 2), pp. S65-S584.

Article from The Burton Report, "Artificial Discs", 5 pages, website at http://www.burtonreport.com/infspine/surgartificialdiscs.htm.

Traynelis, M.D., Vincent, and Haid, JR., M.D., Regis W., "Spinal Disc Replacement: The Development of Artificial Discs", 12 pages.

Bao, Ph.D., Qi-Bin, and Yuan, M.D., Hansen A., "Artificial Disc Technology", Neurosurg Focus 9(4), 2000, 2000 American Association of Neurological Surgeons, 12 pages.

German Search Report for European Application EP 04 72 6859.4; Completed Sep. 21, 2006; Rainer—Berlin; Issued Oct. 4, 2006.

PCT Search Report for PCT EP/2004/006956; Completed Oct. 22, 2004, Mailed Nov. 4, 2004.

* cited by examiner

INTERVERTEBRAL IMPLANT

BACKGROUND OF THE INVENTION

The invention relates to an intervertebral implant with a top contacting element, a bottom contacting element and arranged between these a core which with an upper, spherical bearing surface engages a spherical bearing socket, having the same radius, of the top contacting element and with a lower, spherical bearing surface engages a spherical bearing socket, having the same radius, of the bottom contacting element.

Such an intervertebral implant is known, for example, from U.S. Pat. No. 5,401,269. Herein the bearing surfaces and the associated bearing sockets on the upper side and on the underside of the core have the same radius, i.e., the core is lens-shaped. Pivoting movement of the two contacting elements relative to each other automatically results in a translational movement of the two contacting elements towards each other. Moreover, no defined kinematics are achievable with such an arrangement. For, upon pivoting movement of the contacting elements relative to each other, there are various possibilities of relative movement, depending on whether upon pivoting movement of the two contacting elements relative to each other, the core remains unpivoted in one contacting element and upon pivoting movement only the other contacting element moves relative to the core, whether conversely the core pivots only relative to the one contacting element and remains unpivoted relative to the other contacting element or whether a situation between these arises where both contacting elements are displaced relative to the surface of the core. If the core remains at rest relative to one of the two contacting surfaces during this pivoting movement, the entire movement of the contacting element takes place exclusively around the center point of the bearing surface relative to which the contacting element pivots, i.e., in one case around the center point of the top contacting surface, in the other case around the center point of the bottom contacting surface, and if the core moves relative to both bearing surfaces, an undefined movement results, which is made up of pivoting movements around both center points.

In particular, in order to keep the undesired translational movement as low as possible, it is also known to allow the core to engage on one side only with a spherical bearing surface in a corresponding bearing socket of a contacting element and to provide on the opposing side a plane bearing surface between the core and the other contacting element (U.S. Pat. No. 5,507,816). The core can then deviate laterally on the plane bearing surface and compensate the undesired translation. Owing to the relatively high forces acting by way of the ligaments and muscles on the adjacent vertebral bodies, the vertebral bodies are clamped strongly against one another and, upon pivoting movement of the contacting elements, this may result in the core being driven laterally out of the space between the contacting elements, i.e. the core will possibly move on the plane bearing surface further out of the position of rest than is expedient for the physiological bearing of the vertebral bodies.

The object of the invention is to so design an intervertebral implant of the kind described at the outset that, on the one hand, a defined movement sequence can be ensured and that, on the other hand, the undesired translational movement during the pivoting of the contacting elements is kept as small as possible.

SUMMARY OF THE INVENTION

This object is accomplished in an intervertebral implant of the kind described at the outset in accordance with the invention in that the radius of the bearing surface and of the bearing socket receiving it differs on opposing sides of the core at least by the factor 5.

A core is thus used, which has spherically outwardly curved bearing surfaces on both sides, which engage in corresponding bearing sockets, having the same radius, of the contacting elements, but on one side the radius of this bearing surface is selected so as to be very large, whereas on the other side it is designed in a way similar to that in previously known cores and ensures good pivoting of the contacting elements. On the side on which the bearing surface and the bearing socket have a very large radius the core moves on the surface of the bearing socket similarly to on a plane surface, but a localization of the core in the area of this bearing socket nevertheless results, as the core is pressed into the bearing socket by the high forces clamping the vertebral bodies against one another. A position of rest is thus obtained for the core. However, a pivoting of the core in this bearing socket with a very large radius does not result in any great angular changes between top and bottom implant end plates as the radius is very large.

The factor between the radii of the two bearing surfaces and the two corresponding bearing sockets may be between 4 and 10, in particular, in the range of between 6 and 8.

While the smaller radius lies in the order of magnitude of between 5 and 10 mm, the radii for the bearing surface with the larger radius will lie between 80 and 120 mm. This results in very flat bearing sockets, with the maximum depth of such a bearing socket lying, for example, between 0.2 and 1.0 mm.

It is advantageous for the bearing surface of the core with the larger radius to lie on its underside, but, in principle, the reverse arrangement would also be possible.

In a preferred embodiment of the invention it is provided that the bearing socket with the larger radius is machined in the plane bottom of a recess in the adjacent contacting element.

Use of a spherical bearing socket also has the great advantage that with a conventional turning tool a surface of this bearing socket can be produced, which is machined substantially more precisely than is possible with a milling tool such as normally used for producing a plane bearing surface. The grinding work required during the manufacture is thus reduced, and, in addition, this improved surface structure results in less abrasion during use and, therefore, in higher durability.

It can be provided that the recess in the contacting element is delimited by side walls, and the side walls preferably extend perpendicularly to the bottom of the recess.

In a preferred embodiment the core comprises on two opposing sides lateral guiding surfaces which rest on the parallel side walls of the recess and thereby secure the core against pivoting transversely to the longitudinal direction of the guiding surfaces. By way of such a design the pivoting movement of the core in the bearing socket with a larger radius can be reduced to a pivoting movement which occurs in one direction only, which is preferably the anterior-posterior direction.

Furthermore, stops may be provided for delimiting the pivoting movement of the core in the longitudinal direction of the guiding surface. It is advantageous for these stops to be formed by the side walls of the recess.

When plane bearing surfaces are used between core and contacting element it is also known to delimit the displacing movement by stops. In these cases, the core can be moved in an unbraked manner towards the stops during such displacement, and this results in increased wear. By providing a bearing socket with a large radius as bearing for the core, this movement of the core towards the stops is braked owing to the high forces between the adjacent vertebral bodies during deflection of the core, i.e., in this case the core strikes the stops in a damped manner, and this reduces the wear and thus increases the lifetime of the implant.

It is advantageous for the center point of the bearing socket with the larger radius to lie closer to the anterior side wall of the recess than to the posterior side wall. In the normal state, the core thus rests against the stop of the anterior side wall and upon pivoting of the contacting elements is at the most displaced in posterior direction, but not in anterior direction. This corresponds to the physiological behavior of the vertebral bodies during a pivoting movement.

The spacing of the stops can be between 1 mm and 3 mm larger than the dimensions of the core between its outer sides which come to rest against the stops. The pivoting movement of the core in the bearing socket of larger radius is thus limited to a relatively narrow pivoting range. In this way an undesirably large translation is avoided, but, on the other hand, owing to the pivoting of the core relative to the top and bottom contacting elements it is made possible for the implant to adapt optimally to the respective kinematic requirements.

The spherical bearing surface with the larger radius can extend over the entire cross-sectional area of the core. This can also be the case for the spherical bearing surface of smaller radius.

It is advantageous for the core to have between its two bearing surfaces an outer surface which passes over at an angle into the two bearing surfaces.

The outer surfaces can extend parallel to a connection line between the highest point and the lowest point of the two bearing surfaces.

In a modified embodiment it can be provided that the core has at its posterior end lateral projections which engage under a projection of the recess. A securing of the position of the core in the recess is thereby obtained. In extreme implanting situations and under unphysiological stress, for example, during a fall, the core is thereby secured against snapping out of the recess. The projections on the core can be formed by a stepped formation of the core.

In particular, it can be provided that the core comprises at the posterior end a plate-shaped bottom part whose underside forms the bearing surface with the larger radius, and a disc-shaped top part whose upper side forms the bearing surface with the smaller radius, and that the bottom part projects laterally over the top part and thereby forms the projection on the core.

The bottom part can have a rectangular cross-section with rounded off corners.

The top part preferably has a circular cross-section.

In a particularly preferred embodiment it is provided that the bottom part has a square cross-section with an edge length equal to the radius of the top part. The bottom part thus projects on all four sides in the shape of a crescent over the top part and forms corresponding projections there.

The bottom part can be thicker at the anterior side than at the posterior side.

Bottom part and top part of the core are preferably of one-piece design.

The projection of the recess can preferably be formed by the side wall of a groove which is machined in the recess along the posterior side wall thereof.

BRIEF DESCRIPTION OF THE DRAWINGS

The following description of preferred embodiments of the invention serves in conjunction with the drawings for further explanation. The drawings show.

DETAILED DESCRIPTION OF THE INVENTION

Figure 1:
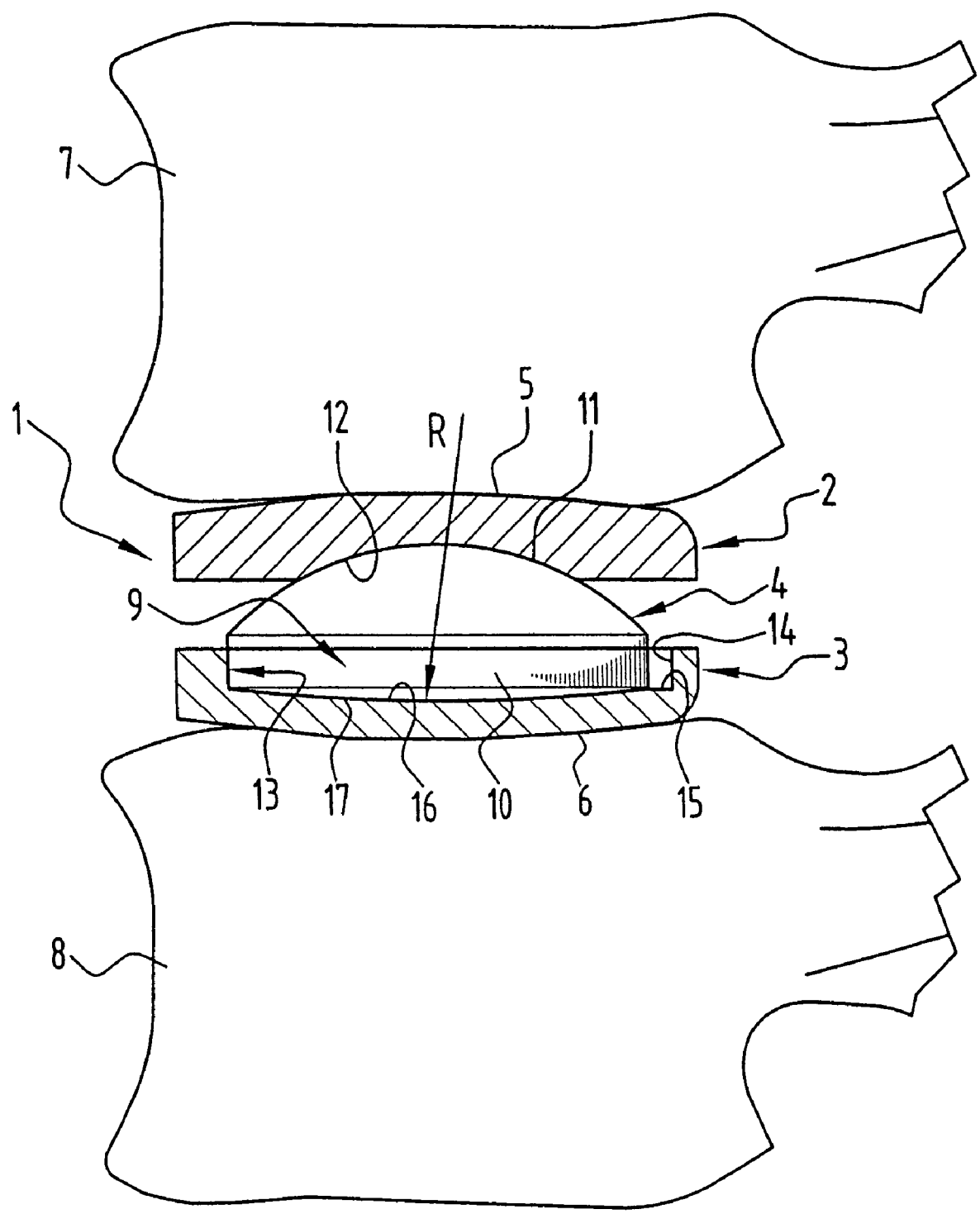
FIG. 1: a side view of an intervertebral implant inserted between two vertebral bodies with contacting elements sectioned in anterior-posterior direction.

The intervertebral implant 1 shown in the drawings comprises a top contacting plate 2 and a bottom contacting plate 3, between which a core 4 is arranged. The two contacting plates 2 and 3 preferably consist of a biocompatible metal, the core 4 of a biocompatible plastic material, for example, of polyethylene. The contacting plates 2 and 3 have on their outer sides facing away from each other contacting surfaces 5 and 6, respectively, which come to rest against the end faces of two vertebral bodies 7, 8, between which the intervertebral implant 1 is inserted instead of the previously removed intervertebral disc.

The one-piece core 4 comprises a plate-shaped central portion 9 with vertical outer surfaces 10. Adjoining the upper side of the central portion 9 is a spherical cap-shaped bearing surface 11, which engages a spherical cap-shaped bearing socket 12 having the same radius on the side of the contacting plate 2 opposing the contacting surface 5, thereby producing a pivotal bearing in this area.

In the side of the contacting plate 3 opposing the contacting surface 6 of the bottom contacting plate 3 a recess 13 is machined, which is delimited on all sides by a vertical side wall 14 and has a flat bottom 15. There is machined in this flat bottom 15 a spherical cap-shaped bearing socket 16, in which a likewise spherical cap-shaped bearing surface 17 of the core 4, having the same radius R and adjoining the central portion 9 on the underside, engages.

The radius of the upper bearing surface 11 and the upper bearing socket 12 is substantially smaller than the radius of the lower bearing surface 17 and the lower bearing socket 16. The ratio of the dimensions is at least 1:5, and preferably lies in the range of between 1:6 and 1:8. For example, the radius of the upper bearing surface 11 and the upper bearing socket 12 may be in the order of magnitude of 15 mm, the radius of the lower bearing surface 17 and the lower bearing socket 16, in contrast, in the order of magnitude of 100 mm. In this way, the depth of the bearing socket 16 is very low, with this depth lying, for example, in the order of magnitude of between 0.2 mm and 1.0 mm.

The side wall 14 of the recess 13 comprises on opposite sides of the recess 13 two parallel, straight-lined sections 18, 19, which extend in anterior-posterior direction of the intervertebral implant 1 and form a guiding surface for the core 4, whose outer surface 10 likewise comprises on opposite sides two flat sections 20, 21 extending parallel to each other. The spacing of these sections 20, 21 corresponds to the spacing of the sections 18, 19, so that the core 4 is received in the recess 13 so as to be displaceable in anterior-posterior direction, but not displaceable transversely thereto. A pivoting of the core transversely to the anterior-posterior direction is, therefore, excluded. A pivoting is only possible in anterior-posterior direction, whereas the top contacting plate 2 is freely pivotable in all directions of the core 4.

This free pivoting movement is limited by the outer surface 10 of the core 4 striking the side wall 14 of the recess 13. Both the side wall 14 and the side wall 10 comprise for this purpose on the anterior side of the intervertebral implant 1 straight-lined sections 22 and 23, respectively, which extend perpendicularly to the sections 18, 19, 20 and 21. On the side opposing the sections 22 and 23, the outer surface 10 and the side wall 14 are of circular design and pass continuously into the sections 18, 19 and 20, 21. The bearing socket 16 in the recess 13 is not arranged exactly at the center in the recess 13, but is slightly displaced in the direction towards the section 22, so that when the section 23 rests against the section 22 the core 4 is in the physiologically correct position between the two vertebral bodies 7 and 8, as shown in FIG. 1. This is the position of rest of the core 4.

Upon pivoting of the two contacting plates 2, 3 relative to each other, the top contacting plate 2 slides substantially on the upper contacting surface 5, with the core 4 initially remaining in its position of rest and only being pivoted in the bearing socket 16 upon stronger pivoting of the contacting plate 2. The bearing socket 16 thus exercises a restoring force, which pivots the core 4 into the position of rest. Nevertheless, the core 4 may, if required, be slightly pivoted in the bearing socket 16 and thereby reduces the translatory displacement of the contacting plates 2, 3 when these are pivoted relative to each other.

The spacing between the section 22 of the bottom contacting plate 3 and the opposing side of the side wall 14 of the recess 13 is slightly larger than the dimensions of the core 4, so that the core 4 may be pivoted slightly out of the position of rest in the bearing socket 16, but the pivoting movement is limited. For example, the spacing between the core 4, on the one hand, and the side wall 14 of the recess 13, on the other hand, may lie in the position of rest of the core 4 between 1 mm and 3 mm.

Figure 2:
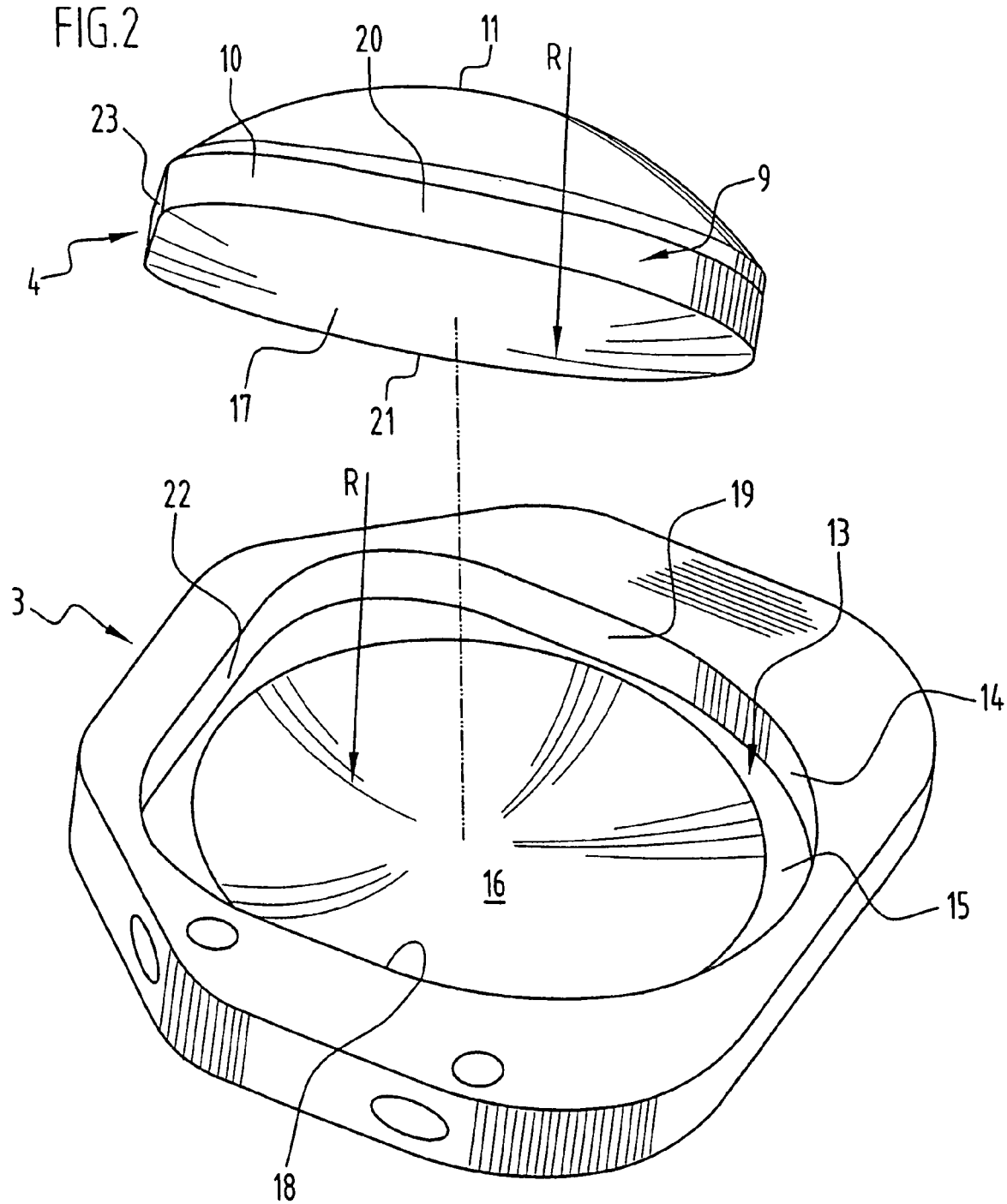
FIG. 2: a perspective view of the bottom contacting element and the core to be inserted therein.
Figure 3:
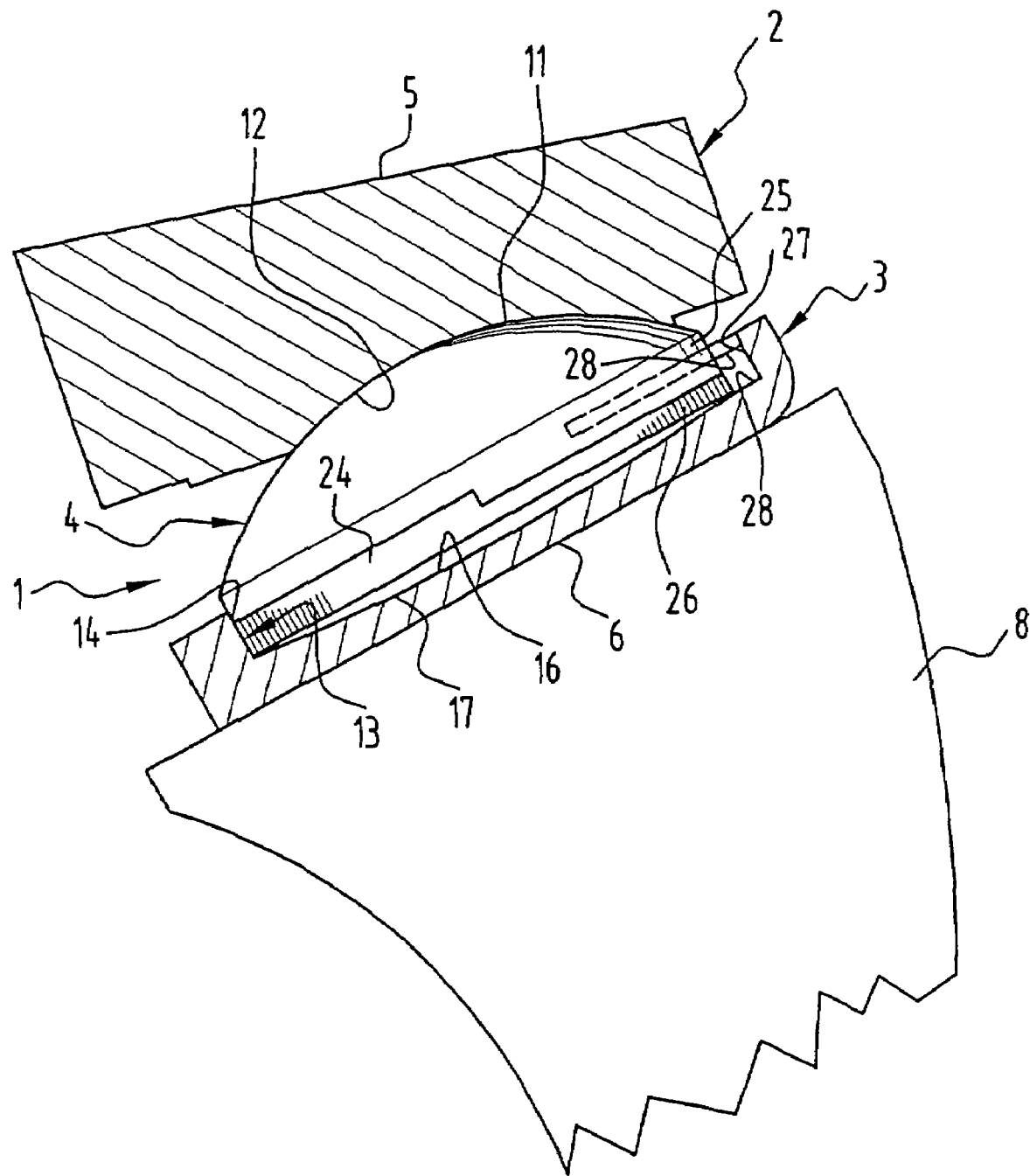
FIG. 3: a schematic side view of a modified embodiment of an intervertebral implant with the contacting elements pivoted to an extreme degree.
Figure 4:
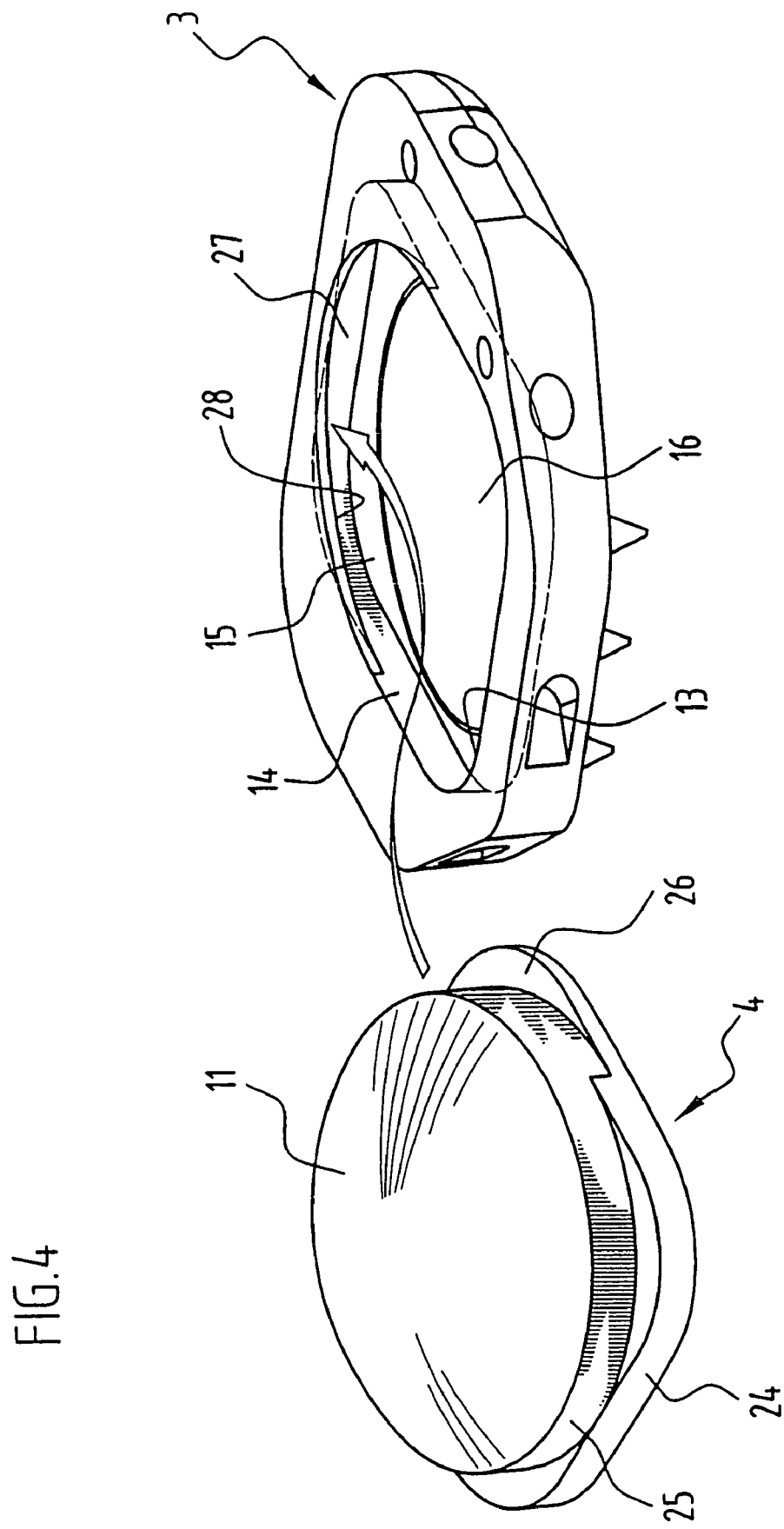
FIG. 4: a perspective view of the intervertebral implant of FIG. 3 prior to insertion of the core into the recess of the bottom contacting element.

The intervertebral implant of FIGS. 3 to 4 is of similar design to that of FIGS. 1 and 2. Therefore, corresponding parts bear the same reference numerals.

In the embodiment of FIGS. 3 and 4, the core is divided into two portions, namely a plate-shaped bottom part 24 and a disc-shaped top part 25. The plate-shaped bottom part 24 has a rectangular cross-section with rounded off corners and is thinner in the posterior portion than in the anterior portion. The top part 25 has a circular cross-section. The radius of the top part 25 corresponds to the edge length of the bottom part 24, so that the disc-shaped top part 25 touches the edges of the square bottom part 24 on all four sides at the center thereof.

In its corner areas, the plate-shaped bottom part 24 therefore protrudes in the shape of a crescent over the top part 25 and forms projections 26 there. The underside of the bottom part 24 is formed by the bearing surface with the larger radius, the upper side of the top part 25 by the bearing surface with the smaller radius.

There is machined in the posterior side wall of the recess 13 a groove 27 which extends along this side wall, so that the bottom 15 passes over into a side wall of this groove 27. The thus enlarged recess 13 is covered by the opposing side wall of the groove 27, which thus forms a projection 28.

When the core 4 is inserted into the recess 13, the projections 26 engage the groove 27 and a securing against unintentional lifting of the core 4 off the bottom contacting plate 3 is thereby ensured. Even in the event of an unphysiological movement which may occur, for example, during a fall, it is thereby ensured that the core will not be able to snap out of its bearing position.

The invention claimed is:

1. An intervertebral implant with a top contacting element, a bottom contacting element, and a core arranged between the top contacting element and the bottom contacting element,
    said core comprising an upper spherical bearing surface for engaging a spherical bearing socket of the top contacting element having a radius substantially equal to a radius of the upper spherical bearing surface of the core, and said core further comprising a lower spherical bearing surface for engaging a spherical bearing socket of the bottom contacting element having a radius substantially equal to a radius of the lower spherical bearing surface of the core, wherein the radius of the lower spherical bearing surface and the radius of the upper spherical bearing surface of the core differ by at least a factor of 5, and wherein the bearing socket with the larger radius is machined in a flat bottom of a recess in the adjacent contacting element.

2. An intervertebral implant with a top contacting element, a bottom contacting element, and a core arranged between the top contacting element and the bottom contacting element,
    said core comprising an upper spherical bearing surface for engaging a spherical bearing socket of the top contacting element having a radius substantially equal to a radius of the upper spherical bearing surface of the core, and said core further comprising a lower spherical bearing surface for engaging a spherical bearing socket of the bottom contacting element having a radius substantially equal to a radius of the lower spherical bearing surface of the core,
    wherein the radius of the lower spherical bearing surface and the radius of the upper spherical bearing surface of the core differ by at least a factor of 5, and wherein the bearing surface of the core with the larger radius lies on its underside,
    wherein the bearing socket with the larger radius is machined in a flat bottom of a recess in the adjacent contacting element.

3. Intervertebral implant according to claim 2, wherein the core comprises lateral projections at its posterior end which engage under a projection of the recess.

4. Intervertebral implant according to claim 3, wherein the projections on the core are formed by a stepped formation of the core.

5. Intervertebral implant according to claim 4, wherein the core comprises a plate-shaped bottom part whose underside forms the bearing surface with the larger radius at the posterior end, and a disc-shaped top part whose upper side forms the bearing surface with the smaller radius, and in that the bottom part protrudes laterally over the top part and thereby forms the projection on the core.

6. Intervertebral implant according to claim 5, wherein the bottom part has a rectangular cross-section with rounded off corners.

7. Intervertebral implant according to claim 5, wherein the top part has a circular cross-section.

8. Intervertebral implant according to claim 5, wherein the bottom part is thicker at the anterior side than at the posterior side.

9. Intervertebral implant according to claim 5, wherein the bottom part and the top part of the core are of one-piece design.

10. Intervertebral implant according to claim 3, wherein the bottom part has a square cross-section whose edge length is equal to the radius of the top part.

11. Intervertebral implant according to claim 3, wherein the projection of the recess is formed by the side wall of a groove which is machined in the recess along the posterior side wall thereof.

12. An intervertebral implant with a top contacting element, a bottom contacting element, and a core arranged between the top contacting element and the bottom contacting element, said core comprising an upper spherical bearing surface for engaging a spherical bearing socket of the top contacting element, and said core comprising a lower spherical bearing surface for engaging a spherical bearing socket of the bottom contacting element, the bottom contacting element having a recess with a flat bottom surface, the spherical bearing socket of the bottom contacting element being formed in the flat bottom surface, wherein the recess is delimited by side walls surrounding the perimeter of the flat bottom surface.

13. Intervertebral implant according to claim 12, wherein the side walls extend perpendicularly to the bottom of the recess.

14. Intervertebral implant according to claim 12, wherein the core has on two opposing sides thereof lateral guiding surfaces, which rest against the parallel side walls of the recess and thereby secure the core against pivoting transversely to a longitudinal direction of the guiding surfaces.

15. Intervertebral implant in accordance with claim 14, wherein the guiding surfaces extend in anterior-posterior direction.

16. Intervertebral implant according to claim 14, wherein stops are provided for delimiting the pivoting movement of the core in the longitudinal direction of the guiding surfaces.

17. Intervertebral implant according to claim 16, wherein the stops are formed by the side walls of the recess.

18. Intervertebral implant according to claim 16, wherein a center point of the bearing socket in the bottom contacting element lies closer to an anterior side wall of the recess than to a posterior side wall.

19. Intervertebral implant according to claim 16, wherein spacing of the stops is from 1 to 3 mm larger than dimensions of the core between outer sides of the core which come to rest against the stops.

20. Intervertebral implant according to claim 13, wherein the core has on two opposing sides thereof lateral guiding surfaces, which rest against the parallel side walls of the recess and thereby secure the core against pivoting transversely to a longitudinal direction of the guiding surfaces.

* * * * *